United States Patent [19]

Ruben

[11] Patent Number: 5,581,409
[45] Date of Patent: Dec. 3, 1996

[54] IMAGING SYSTEM TO COMBINE DISPARATE FIELDS OF VIEW

[75] Inventor: Paul L. Ruben, Penfield, N.Y.

[73] Assignee: Republic Lens Co., Inc., Englewood, N.J.

[21] Appl. No.: 324,183

[22] Filed: Sep. 30, 1994

[51] Int. Cl.$^6$ ................................................. G02B 27/14
[52] U.S. Cl. ......................................... 359/636; 359/638
[58] Field of Search ............................... 359/636, 638, 359/640, 831, 833, 837, 619, 620, 621

[56] References Cited

U.S. PATENT DOCUMENTS

| | | | |
|---|---|---|---|
| 4,024,573 | 5/1977 | Carnes | 358/87 |
| 4,465,937 | 8/1984 | Forbes | 250/560 |
| 4,485,406 | 11/1984 | Brownstein | 358/227 |
| 4,660,091 | 4/1987 | Nutting | 358/214 |
| 4,787,725 | 11/1988 | Preussner | 359/401 |
| 4,906,099 | 3/1990 | Casasent | 356/394 |
| 4,963,962 | 10/1990 | Kruegle | 358/108 |
| 5,495,370 | 2/1996 | Tuffen | 359/402 |

*Primary Examiner*—Georgia Y. Epps
*Assistant Examiner*—Ricky Mack
*Attorney, Agent, or Firm*—Spencer T. Smith

[57] ABSTRACT

A lens system is provided which has a plurality of lens systems each having a Dove prism and a lens for imaging the light received from its Dove prism on the image field of a CCD camera. Each lens system views a different scene and images that scene on a different portion of the image field. The Dove prisms rotate the scenes so that they can be of maximum size on the image field.

15 Claims, 3 Drawing Sheets

| CHANNEL | Ψ (DOVE TILT) | θ (DOVE ROTATION) |
|---|---|---|
| 1 | $\Psi_{BB'} = 2.487°$ | 0° |
| 2 | $\Psi_{BB} = .11°, \Psi_x = -2.810°$ | 45° |
| 3 | $\Psi_{BB'} = -.11°, \Psi_x = 2.810°$ | -45° |
| 4 | $\Psi_{BB'} = 2.487°$ | 90° |

NOTE: Ψ PIVOTS ABOUT LENS VERTEX 3.

| CHANNEL | Ψ (DOVE TILT) | Θ (DOVE ROTATION) |
|---|---|---|
| 1 | $\Psi_{BB'} = 2.487°$ | 0° |
| 2 | $\Psi_{BB'} = .11°, \Psi_X = -2.810°$ | 45° |
| 3 | $\Psi_{BB'} = -.11°, \Psi_X = 2.810°$ | -45° |
| 4 | $\Psi_{BB'} = 2.487°$ | 90° |

IMAGING SYSTEM TO COMBINE DISPARATE FIELDS OF VIEW

The present invention relates to two-dimensional (CCD—charge coupled device or electronic image sensor) cameras which can be used to survey or inspect a scene defined by the sight area of the camera.

As the size of the scene to be surveyed increases, the image on the sensor of the camera progressively becomes smaller with a concomitant loss of detail. This may render the surveillance of little value. When the acquired detail is not adequate, whether for visual or electronic evaluation, a plurality of cameras can be used each dedicated to a specific subscene within the scene. This increases the cost of the surveillance and is undesirable.

It is accordingly an object of the present invention to provide a lens system which, using a single camera, can increase the detail in such subscenes relative to the degree of detail presently achievable when the camera surveils the entire scene.

Other objects and advantages of the present invention will become apparent from the following portion of this specification and from the accompanying drawings which illustrate in accordance with the mandate of the patent statutes a presently preferred embodiment incorporating the principles of the invention.

Referring to the drawings.

The effectiveness of the seal of a capped bottle is largely dependent on the quality of the top or sealing surface on the rim of the bottle. If this sealing surface has a transverse scratch, for example, the seal may be defective. Conventionally, a two-dimensional camera views the sealing surface of the rim of a standing bottle so that an electronic analysis can be undertaken to identify surface flaws. The electronic image sensor 10 of such a camera is shown schematically in FIG. 1 as is the sealing or top surface of the rim 12 of a bottle to be inspected. The field of the electronic image sensor 10 is substantially rectangular in area while the image of a selected scene 14 in which the top surface of the rim is located is square.

Figure 1:
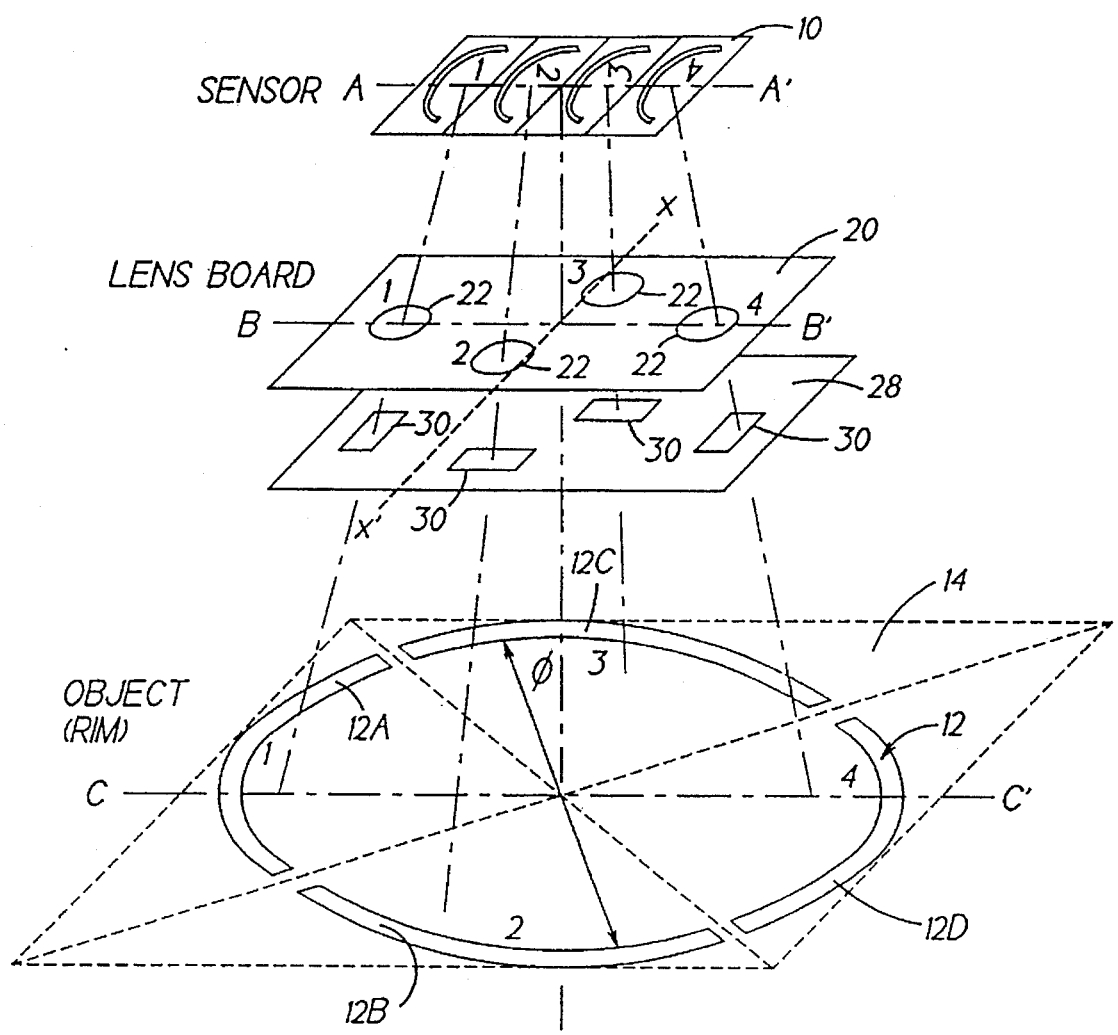
FIG. 1 is a schematic illustration of the multi-imager lens system made in accordance with the teachings of the present invention.
Figure 2:
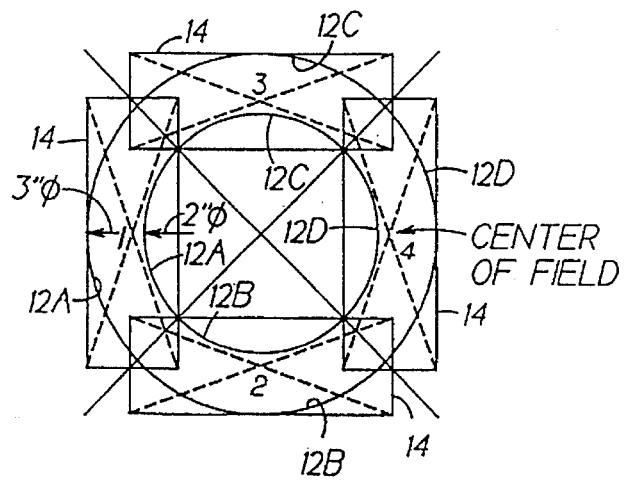
FIG. 2 is a top view showing two circles representing 2 and 3 inch diameter rims of a container or the like and four rectangular fields which will be imaged by the multi-lens system.

To enhance the detail of the sealing surface, the sealing surface is arbitrarily broken up into a plurality of annular segments (here four—12A, 12B, 12C, 12D). The four segments can be presented with maximum magnification within the field of the image sensor by presenting the four segments as shown in FIG. 1 with the width of each subfield one quarter of the dimension of the field in the A—A' direction and the length of each subfield equal to the dimension of the image field in the transverse direction. The ratio of width to length of one of these subfields can be referred to as the subfield aspect ratio. FIG. 2 illustrates how a subscene or field 14, having that aspect ratio can completely enclose one of the four rim segments 12A, 12B, 12C, 12D, where the rim has a diameter of from just above 2" to 3" in diameter. The center of the field is indicated in the fields.

Figure 4:
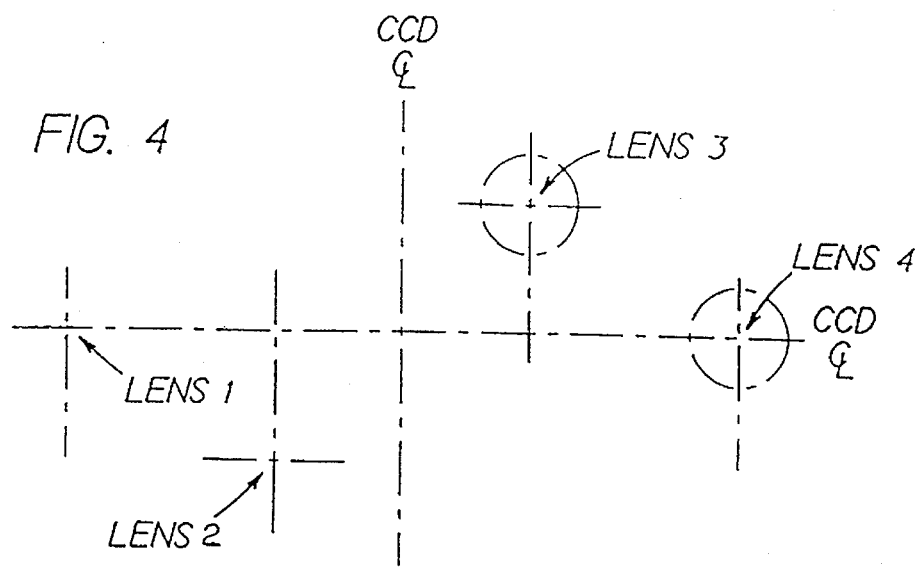
FIG. 4 is a schematic top view of the lens board shown in FIG. 1 showing the relative positions of the individual lens systems which make up the multi-imager lens system.
Figure 5:
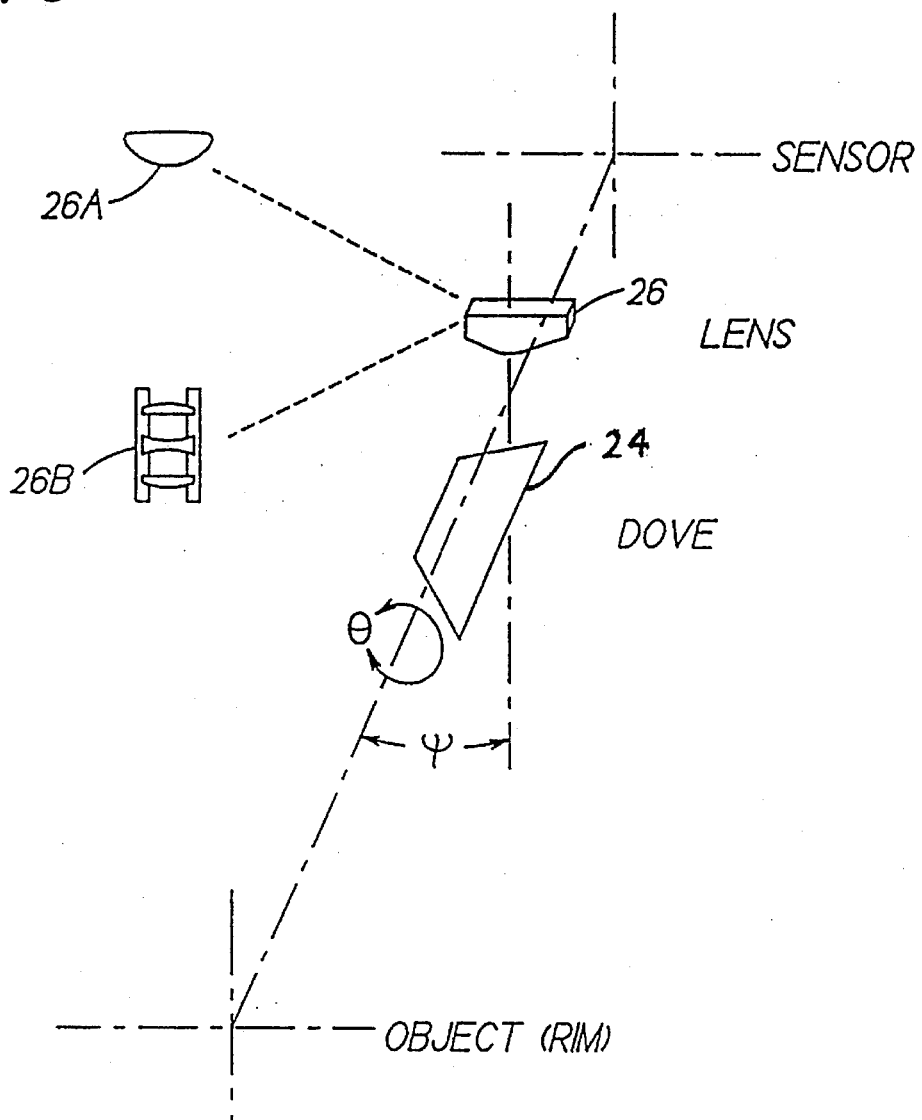
FIG. 5 is a schematic illustration of one of the lens systems.

A lens board 20 of a lens secured to the two-dimensional camera supports four lens systems 22 which image the four subscenes in the four subfields. The numbers (channels) 1, 2, 3 and 4 are used in the drawings to correlate the subscenes, subfields and lens systems. Each lens system 22 (FIG. 4) includes one Dove prism 24 to adjust the image orientation through 360 degrees and a lens assembly, which in the preferred embodiment is a doublet lens. While a doublet lens 26 is preferred it may also be a singlet lens 26A or a three element lens 26B. Optionally, a field stop plate 28 having a hole 30 having the same shape as the shape of the associated field, for each lens system may be located between the Dove prism and the object plane to limit and define the field of view. If required, a first surface mirror 29 or other plano reflecting surface may be associated with any or each lens system for pointing.

Figure 3:
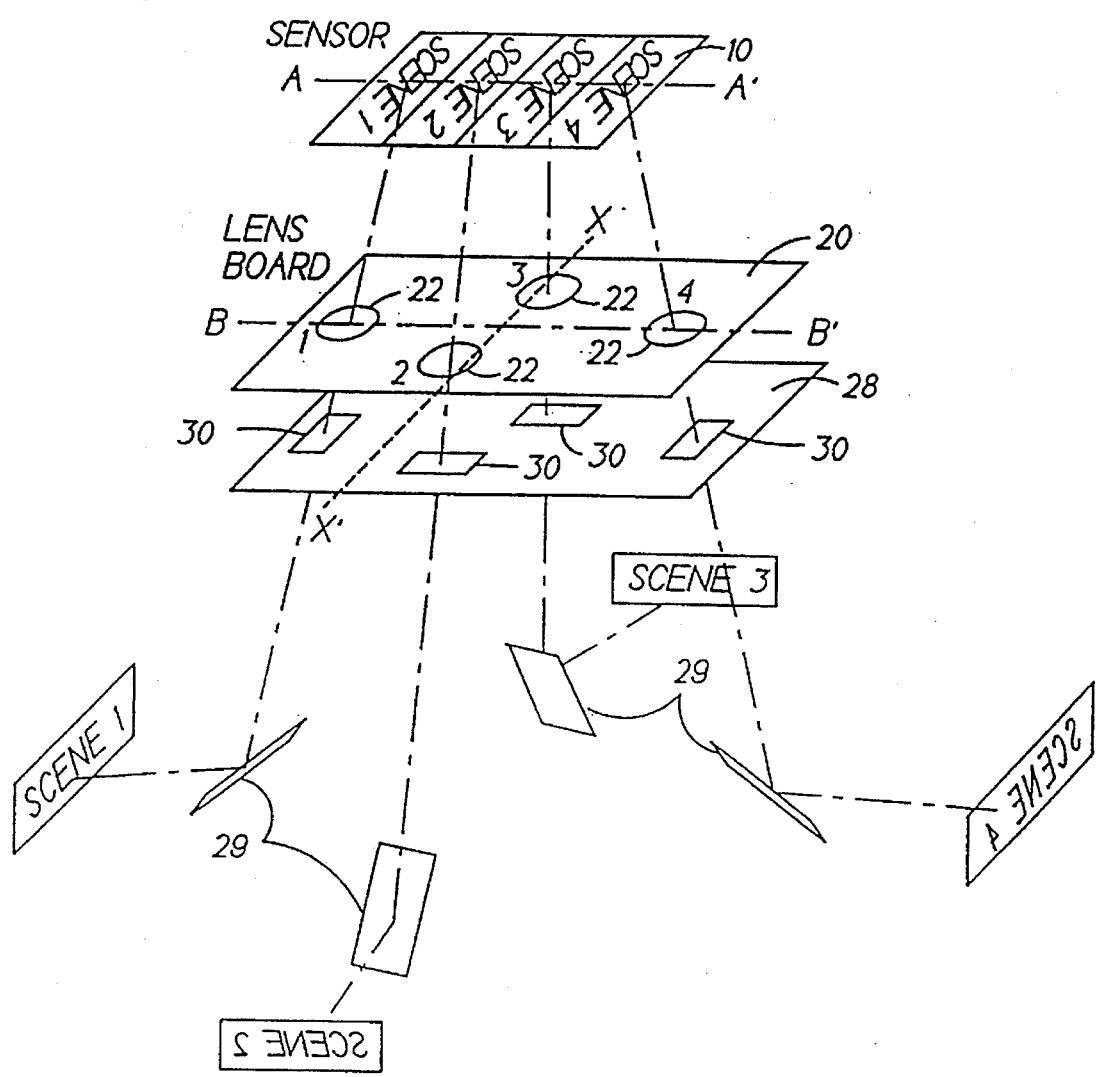
FIG. 3 is a view similar to FIG. 1 wherein individual mirrors are used to aim at the surveyed scenes.

The number of lens systems used with a given size sensor is limited by two considerations: the number of images desired on a single sensor and the diameter of the lens, determined by the focal length, f-number, and required field coverage or field angle, which may not be so great that the lenses occupy the same space (see FIG. 3 for relative positions of the lens systems). The optical axes of the doublet lenses are parallel to each other and perpendicular to the sensor field but are displaced from the axis perpendicular to image plane of the receptor (sensor) and through its center. Each Dove prism is tilted about the effective stop position of its optical system along the principal ray connecting the center of that segment of the receptor (image field) upon which the object field is recorded to the center of the object field. This is so that the center of the object (or image) field of the individual optical system may be rotated without displacement by rotating the Dove prism. The rate of rotation of the image field is twice the rate of rotation of the prism. Mirrors may be used to deflect the line of sight of each channel by 90 degrees, plus or minus 45 degrees. Rotated images caused by the mirrors can be restored by rotation of the Dove prisms. Multiple lens systems have been used for many years in the school picture industry. In that application, photographic portraits are made in different sizes on a single sheet of photographic printing paper using a single film negative. This is accomplished by using two or more lenses (of the same or different focal lengths), displaced from an axis perpendicular to the center of the negative, to image the portrait from the negative onto the paper. It creates several images from one object. No prisms or mirrors are used.

In the preferred embodiment, four optical systems are employed to image four quadrants of a contiguous object field (rim of glass bottle). Each system consists of an f/12.5 cemented glass doublet of 50 mm focal length and a Dove prism 15.73×3.72×3.72 mm. Where the fields are at varying distances from the sensor, different focal length lenses may be used in each channel to provide different object magnifications. The four doublet lenses are positioned on a plane 53.44 mm in front of the receptor, so that the receptor is at their common plane of best image focus. The optical axes of the four doublet lenses are laterally displaced from the axis perpendicular to image plane of the receptor (sensor) and through its center. Each lens is so positioned that the "center of field" is imaged in the desired portion of the sensor. To reconstruct the geometry of this positioning, first note that the aspect ratio of the sensor is 3:4. The sensor is divided into four image fields, each having a 3:1 aspect ratio. The object field also has a 3:1 aspect ratio. The ratio of the object distance to the image distance, or system magnification, is 9.5:1, and this ratio determines the ratio between the displacement of the optical axis of each lens with respect to the center of the field and image segment center. The principal ray must describe a straight line from the center of the object field through the nodal points of the lens to the center of the divided image field. It must appear to go through the Dove prism undeviated, which is why the prism is tilted about the effective stop position. To insure that the principal ray goes through the Dove prism undeviated, each prism is tilted about the effective stop position of the system, determined by where the principal ray of the beam crosses the optical axis of the lens, near, but not necessarily at the front surface of the prism, and not necessarily at the lens vertex. The lens formula is as follows:

| EF 50.00 | | | F/NO. F/12.50 1/MAG. 9.500× |
|---|---|---|---|
| SURFACE | RADIUS | THICKNESS | GLASS $N_D$ $V_D$ |
| 1 (DOVE IN) | PLANO | 17.907 | 1.517–64.2 |
| 2 (DOVE OUT) | PLANO | 3.000 | |
| 3 (LENS IN) | 20.4320 | 0.800 | 1.617–36.6 |
| 4 (LENS INTERMEDIATE) | 9.65052 | 1.400 | 1.517–64.2 |
| 5 (LENS OUT) | PLANO | | |

The image falling on the image sensor can be evaluated visually or automatically with the use of a computer as in the preferred embodiment, where bottles are to be inspected. Such a computer can be connected to a reject mechanism for removing a bottle when it fails inspection (a jet of air can blow the bottle off of the conveyor carrying it away from the machine in which it was made).

By introducing a first surface mirror before each Dove prism, the field of view may be deflected. No longer is the system imaging four quadrants of a contiguous object plane, but four different scenes in space. Each mirror may be pivoted plus or minus 22.5 degrees with respect to the principal ray of the system, resulting in a pointing variation of plus or minus 45 degrees. Each mirror may also be rotated 360 degrees about the principal ray to provide pointing flexibility. The orientation of the object can then be adjusted by rotating the Dove prism. Each lens will be refocussed if the object distance is varied.

The invention achieves the following advantages. 1. It is of relatively simple construction and therefore inexpensive. 2. The object fields may be segments of one larger field or an assembly of several different fields. For example, the field may consist of several portions of a circular object (the preferred embodiment) or the field may be different stations within a room, such as bank teller windows, casino gaming tables, or showcases and merchandise displays in a department store. 3. Using the present four-lens system, specific portions of an object (the bottle rim) in four quadrants of a plane can now be arranged in a nestled fashion and can thus be simultaneously inspected on a single television monitor at a one-third greater magnification than was previously possible using a single lens system. This improves the ability to inspect. 4. Used with mirrors, two or more areas can be monitored with one camera and one TV screen, thus saving the expense of additional sensors, cameras and screens. 5. Different focal length lenses can be used in different channels, thus providing flexibility in scene magnification from a single camera location.

I claim:

1. A multi-image surveillance system comprising
   a two-dimensional camera having an electronic sensor defining a sensor field and
   means for imaging a selected number of different scenes onto a corresponding number of different portions of said sensor field including a corresponding number of lens systems each having
   a Dove prism for viewing one of said scenes, and
   lens means for imaging the light received from said Dove prism onto one of said portions of said sensor field.

2. A multi-image surveillance system according to claim 1, wherein the axis of at lease one of said Dove prisms is tilted with respect to the optical axis of the lens means receiving light from the tilted Dove prism.

3. A multi-image surveillance system according to claim 2, wherein the axis of each of said Dove prisms is tilted with respect to the optical axis of the lens means receiving light from said Dove prism.

4. A multi-image surveillance system according to claim 3, wherein the axes of said lens means are parallel to each other and perpendicular to said sensor field.

5. A multi-image surveillance system according to claim 4, wherein each of said lens means comprises a doublet lens.

6. A multi-image surveillance system according to claim 4, wherein each of said lens means comprises a singlet lens.

7. A multi-image surveillance system according to claim 4, wherein each said lens means comprises a three element lens.

8. A multi-image surveillance system according to claim 4, wherein said different scenes comprise different segments of the annular sealing surface of a bottle rim.

9. A multi-image surveillance system according to claim 8, wherein said different portions of said sensor field fill said sensor field.

10. A multi-image surveillance system according to claim 9, wherein there are four identically shaped portions of said sensor field.

11. A multi-image surveillance system according to claim 10, wherein said four identically shaped portions of said sensor field are parallel.

12. A multi-image surveillance system according to claim 5, wherein the focal length of all of said doublet lenses is the same.

13. A multi-image surveillance system according to claim 12, wherein each of said Dove prisms and doublet lenses are constructed according to the following parameters:

| | | | GLASS | |
|---|---|---|---|---|
| SURFACE | RADIUS | THICKNESS | $N_D$ | $V_D$ |
| 1 | PLANO | 17.907 | 1.517 | 64.2 |
| 2 | PLANO | 3.000 | | |
| 3 | 20.4320 | 0.800 | 1.617 | 36.6 |
| 4 | 9.65052 | 1.400 | 1.517 | 64.2 |
| 5 | PLANO | | | |

14. A multi-image surveillance system according to claim 5, further comprising a field stop plate intermediate said doublet lenses and said scenes including a hole for each doublet lens for limiting and defining the field of view of said doublet lenses.

15. A multi-image surveillance system according to claim 1, further comprising an aiming mirror located intermediate at least one of said Dove prisms and the scene observed by said Dove prism for redirecting the image of the scene to said Dove prism.

* * * * *